United States Patent [19]

Zetlmeisl et al.

[11] Patent Number: 4,877,578
[45] Date of Patent: Oct. 31, 1989

[54] CORROSION INHIBITORS

[75] Inventors: Michael J. Zetlmeisl; William F. Fahey, both of St. Louis, Mo.

[73] Assignee: Petrolite Corporation, St. Louis, Mo.

[21] Appl. No.: 717,916

[22] Filed: Mar. 29, 1985

[51] Int. Cl.⁴ .................. C23F 11/12; C23F 11/14
[52] U.S. Cl. ........................ 422/14; 208/47; 252/390; 252/394; 252/396; 422/16; 210/698
[58] Field of Search ............... 422/14, 16; 252/387, 252/390, 394, 396; 208/47; 210/698

[56] References Cited

U.S. PATENT DOCUMENTS 3,294,705 12/1966 Kautsley ........................ 208/47
3,770,377 11/1973 Scott et al. .................... 422/16

Primary Examiner—Barry S. Richman
Assistant Examiner—Jill Johnston
Attorney, Agent, or Firm—Robert E. Wexler

[57] ABSTRACT

Water soluble corrosion inhibitors which exhibit low hydrocarbon carryunder are prepared by reaction of alkylenepolyamines and formaldehyde.

19 Claims, No Drawings

CORROSION INHIBITORS

BACKGROUND OF THE INVENTION

1. Field of the Invention

This invention pertains to water soluble corrosion inhibitors and use thereof in oil refineries and in other chemical industry processes, particularly in oil refinery water systems. More particularly, the invention relates to polyamine/formaldehyde reaction products as corrosion inhibitors in refinery overhead systems.

Aqueous condensates in refinery overhead systems are extremely corrosive due to the presence of hydrochloric acid from the hydrolysis of chloride salts indigenous to crude oil composition and other corrosive agents. Varying degrees of corrosion protection have been effected by the use of a variety of known oil soluble and water soluble inhibitors. Because such inhibitors generally have a relatively high degree of surface activity, their use can cause oil carryunder from the refinery overhead system into the accumulator water where it can cause a variety of problems downstream. Accordingly there is a need for corrosion inhibitors for chemical process water systems, e.g. refinery overhead systems, which do not cause emulsions which lead to oil carryunder.

2. Prior Art

The use of amines and polyamines and their reaction products with acids as corrosion inhibitors is well known. Examples of a large body of published information includes:

U.S. Pat. No. 3,280,097 discloses reaction products of amines, phenols and aldehydes as corrosion inhibitors in refineries;

U.S. Pat. No. 3,294,705 discloses acid amides of alkylene polyamines as corrosion inhibitors in refineries;

U.S. Pat. No. 3,649,167 discloses morpholine as a corrosion inhibitor in refineries;

U.S. Pat. No. 3,762,873 discloses polyalkylenesuccinimides as corrosion inhibitors in refineries;

U.S. Pat. No. 3,819,328 discloses alkylenepolyamines as corrosion inhibitors in refineries;

U.S. Pat. No. 4,062,764 discloses alkoxyalkylamines as corrosion inhibitors in refineries.

Ger. Offen. No. DE 3136298 discloses quaternaries of alkoxylated alkylenepolyamines as corrosion inhibitors in petroleum recovery;

Richmond et al., Mater. Perform., 21(11), 45–51 disclose the use of amines to prevent corrosion in crude column overheads;

Little et al., Hydrocarbon Process., 56(5), 205–7, disclose control of corrosion in crude unit overheads by an oil-soluble blend of neutralizing amines;

Nathan et al., Corr./74, Int. Corros. Forum, 124/1–124/13 disclose use of neutralizing and film-forming primary and secondary amines as corrosion inhibitors in refinery overhead streams;

Kato et al, Proc. Int. Congr. Met. Corros., 5th, Meeting Date 1972, 967–71, disclose alkylenepolyamines, piperazine and morpholine as corrosion inhibitors in overhead lines.

Although such prior publications disclose a variety of amines as corrosion inhibitors in refinery overhead systems, none address the problem of hydrocarbon carryunder as a result of the emulsifying tendencies of water soluble amine corrosion inhibitors.

SUMMARY OF THE INVENTION

In accordance with the present invention, it has unexpectedly been found that water soluble reaction products of alkylenepolyamines and formaldehyde afford a high degree of corrosion resistance in chemical industry water systems, such as refinery overhead systems, with a minimal amount of emulsion formation which results in hydrocarbon carryunder.

DESCRIPTION OF THE PREFERRED EMBODIMENTS

Prior to the unexpected findings of the invention, it had been generally accepted knowledge that corrosion inhibition and hydrocarbon carryunder are inseparable. That is, a material affording good corrosion inhibition also causes hydrocarbon carryunder. Conversely, it has been generally accepted that a material affording low corrosion inhibition also causes minimal hydrocarbon carryunder.

Contrary to such generally accepted knowledge, the compounds of the present invention surprisingly have been found to afford a high degree of corrosion inhibition while causing minimal hydrocarbon carryunder. It has been found that the compounds of the invention provide good corrosion inhibition without causing emulsification of hydrocarbons into refinery water systems undergoing considerable shear.

The corrosion inhibitors of the invention are prepared by reacting alkylenepolyamines and formaldehydes.

The polyamines useful in the preparation of the inhibitors of the invention are aliphatic polyamines represented by the formula

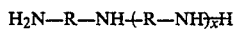

$$H_2N-R-NH+R-NH)_xH$$

wherein R represents a hydrocarbon radical of up to about twelve carbon atoms and x represents 0 to about 15. The hydrocarbon radical may be straight or branched chain, e.g. ethylene, methylethylene, phenylethylene and may be substituted by any organic radical which does not react with formaldehyde, e.g. halo such as chloro, bromo or fluoro and alkylamino or amino. As a practical matter, however, the hydrocarbon radical is preferably straight chain lower alkylene, e.g. ethylene or propylene, and any substituent thereon is preferably lower alkyl, e.g. methyl, ethyl. The hydrocarbon radical may also be derived from fatty materials such as tallow and stearin.

Representative polyamines include ethylenediamine, propylenediamine, diethylenetriamine, triethylenetetramine, tetraethylenepentamine, tetrabutylenepentamine, pentaethylenehexamine, hexaethyleneheptamine, hexapentyleneheptamine, heptaethyleneoctamine, octaethylenenonamine, nonethylenedecamine, decaethyleneundecamine, decahexyleneundecamine, undecaethylenedodecamine, dodecaethylenetridecamine, tridecaethylenetetradecamine, N-tallow propylenediamine and higher polyamines.

In general, the compounds of the invention are prepared by the exothermic reaction of an alkylenepolyamine, e.g. diethylenetriamine, and formaldehyde. The reaction is cooled during addition of the reactants and maintained at about 50°–60° C. The reaction occurs over a period of approximately one hour at which time a temperature drop indicates the reaction is complete. The resultant reaction mixture is a complex mixture including, for example, alkylene-bridged diethylenetriamines.

In general, the corrosion inhibitors are injected into, or otherwise added to, the refinery water system in batch or continuous manner. The amount added is a small but effective corrosion inhibiting amount, for example, from about 20 ppm to about 200 ppm based on the weight of the polyamine, preferably from about 40 to about 120 ppm, more preferably from about 80 to about 120 ppm, especially from about 100 to about 120 ppm.

The corrosion inhibitors may be added neat or diluted with water and may be formulated or blended with other materials or additives generally found useful in refinery systems, for example, simple amines used as neutralizers, algaecides, bactericides, anti-scale agents, detergents and sequestering agents and similar additives.

The following examples will serve to illustrate specific embodiments of the invention and the best mode of practice thereof but are not to be considered as a limitation of the scope thereof.

Examples 1 through 10 illustrate preparation of the inhibitors of the invention. Examples 11 and 12 illustrate the utility and efficiency of the inhibitors as regards the dual requirements of corrosion inhibition and low hydrocarbon carryunder. Example 13 illustrates a field test.

EXAMPLE 1

Diethylenetriamine (14.54 g) was heated to 50° C. in isopropyl alcohol (12.41 g) while stirring in a three-necked round bottom flask. When the temperature stabilized, formaldehyde (35.32 g of a 37% aqueous solution) was added from a dropping funnel. Since the reaction is exothermic, the reaction flask was cooled to 50°-60° C. during addition. After the formaldehyde had all been added, the reaction was stirred at 50°-60° C. for another 15 minutes, and then cooled. At this point the chemical is 32.1% active, based on the amount of formaldehyde and diethylenetriamine added. It can be diluted with water as desired.

EXAMPLES 2-10

In accordance with the procedure of Example 1, the following polyamines are reacted with formaldehyde:

| Example 2 | triethylenetetramine |
| Example 3 | tetraethylenepentamine |
| Example 4 | N—tallow propylenediamine |
| Example 5 | dipropylenetriamine |
| Example 6 | 9-amino-10 hydroxystearylamine |
| Example 7 | propylenediamine |
| Example 8 | tributylenetetramine |
| Example 9 | ethylenediamine |
| Example 10 | tetrapropylenepentamine |

The following examples present data obtained from corrosion tests and hydrocarbon carryunder tests. A description of the tests used is as follows:

CORROSION TESTS

Description of Apparatus

A one liter resin pot with a stopcock on the bottom was the basic reaction vessel for both the flush mounted probe (FMP) and weight loss experiments. A 35/25 ball joint was mounted into the side of the vessel near the bottom. The top of the resin pot had three 24/40 ground glass joints, one for the stirrer bearing, one for a rubber septum for injection of small amounts of material, and the third for a gas impinger with a sparge tube on the inlet and the outlet attached to a bubbler filled with mineral oil. There was also a 10/30 joint for a thermometer. Temperature was controlled at 65° C. with an $I^2R$ Thermowatch connected to a heating mantle and an ASTM 15° C. thermometer ($-2°$ to 80° C.). The charge to the pot was stirred at 400 rpm with a stirring motor attached through a sealed bearing to a teflon agitator (turbine type).

Description of Electrolyte and Hydrocarbon

Isopar M (Exxon) was used as the hydrocarbon phase after depolarizing it by passing it through a 2 liter separatory funnel about ⅓ filled with a coarse mesh activated alumina. Deionized water made about 0.1M in $Na_2SO_4$ is the aqueous phase. Generally, 300 ml hydrocarbon and 600 ml aqueous electrolyte were used. To this was added 0.65 gm $NH_4Cl$, enough to make the aqueous phase 0.02M in $NH_4Cl$. About 25 mg $H_2S$ was also added from a saturated solution prepared by bubbling $H_2S$ into a septum sealed bottle filled with de-aerated water. These $H_2S$ solutions always had about 2500 ppm $H_2S$.

Description of an FMP Test

A laboratory FMP consisted of a standard 1 $cm^2$ inner rod of mild steel as reference electrode, a middle tube of mild steel concentric to this rod for the test electrode, and an outer sleeve of stainless steel tubing for auxiliary. The probe was filled with metallagraphic epoxy and a three lead canon plug was used for connection to monitoring equipment. Small pieces of insulated wire connected the plug to the three electrodes. The overall dimensions of an FMP were one inch in diameter and about six inches in length. The test electrode face was one $cm^2$. The probe was attached to the vessel by slipping it into a glass sleeve with a 35/25 socket, which in turn could be attached to the 35/25 ball on the side of the vessel. Leakage was prevented by wrapping the probe with teflon tape about 1 inch from the end and forcing it into the sleeve.

In a typical experiment with the FMP the probe face was polished with 600 grit polishing paper and mounted in the side of the vessel. The water and hydrocarbon were added through the 24/40 joint where the septum goes. After the system was in place heating, stirring, sparging (with Ar at about 0.5 l/min) and PAIR meter monitoring began. After about 1-2 hours of sparging at 65° C. the observed corrosion rates were 8-10 mpy. A few mls of solution drawn off the bottom through the stopcock measured about pH=8-9. An $O_2$ measurement was made by inserting a piece of tygon into the outlet tube from the stopcock, bleeding a few mls of solution, inserting a sealed Chemet vial into the tygon, bleeding a bit more solution until the tygon had no bubbles, and then snapping the top off the Chemet for colorimetric $O_2$ indication by comparison with standards. In every case $O_2$ was 100 ppb or less. Next, $NH_4Cl$ and $H_2S$ were added as aqueous solutions and inhibitor was added neat. A stock solution of $NH_4Cl$ was prepared such that a 10 ml aliquot contained 0.65 gm $NH_4Cl$. $H_2S$ (25 mg) was added by drawing a 10 ml aliquot of $H_2S$ saturated solution into a syringe and injecting the solution through the septum. After $H_2S$ was added, sparging had to be discontinued. $H_2S$ was added to simulate $H_2S$ in the refinery system. Inhibitor was added neat after the corrosion rates had settled down somewhat. The rates were monitored overnight.

At the end of a test the stirrer was turned off and a qualitative evaluation was made of how quickly and completely the two phases separated. 50 Ml of the aqueous phase was saved for final pH measurement and $H_2S$ determination by the standard thiosulfate method.

Description of Weight Loss Tests

Standard 9 $cm^2$ mild steel electrodes were rinsed thoroughly with acetone, dried in a dessicator, weighed and mounted in a triangular arrangement in a #4 neoprene stopper on one end of one foot long threaded rods coated with teflon. The vessel was charged with 666 ml 0.1M $Na_2SO_4$ for the aqueous phase plus 333 ml isopar M, previously depolarized by passing it through coarse mesh activated alumina. The pot was stoppered and sparged for one hour with Ar (0.5 l/min.), and heated to 65° C. After one hour the electrodes were inserted. Sparging with Ar continued for another hour, and monitoring by means of linear polarization measurements was commenced, using Petrolite Instruments Model 6000 PAIR® meter. After this second hour of Ar sparge 0.65 gm $NH_4Cl$ plus inhibitor (where applicable) was added. The Ar sparge was stopped and the system was sparged with 1% $H_2S$ in Ar. In order to keep pH conditions constant from test to test, the unquaternized compounds were neutralized to a pH of less than 7 before addition.

At the end of the test the electrodes were cleaned, and weight loss was measured from which depth of penetration was calculated. The average PAIR (linear polarization reading) was also determined. The final pH of the aqueous phase was measured. Corrosion rates were calculated in mpy from weight loss using standard calculations.

EMULSION (HYDROCARBON CARRYUNDER) TEST

Description of the Test

A pair of closely matched 125 ml separatory funnels containing 50 ml aqueous phase (0.01M $NH_4Cl$) plus inhibitor and 25 ml hydrocarbon phase (Isopar M) are shaken horizontally on a Burrel wrist action shaker for 5 minutes. Separation times are measured from the immediate cessation of the shaking. At one minute a 10 ml aliquot is drawn from each separatory funnel into 10 ml graduate cylinders and discarded. At 1.5 minutes the 10 ml samples to be analyzed are taken and transferred to milk dilution bottles. At 4.5 minutes another 10 ml is discarded, and the final 10 ml samples are taken at 5 minutes, and saved in milk dilution bottles.

The water samples are analyzed for oil content by the standard oil in water technique, based on infrared absorbance of the CH stretching frequency. The method involves extraction of the water sample into freon (1,1,2 trichloro-1,2,2 trifluoroethane) followed by reading the absorbance on the Miran I IR analyzer and comparing the absorbance to a standard curve with a range from 0–1000 ppm.

Twenty ml freon are added to each milk dilution bottle after the pH of the samples has been adjusted to 5 or lower. The bottles are shaken in pairs for a minute in each hand and allowed to settle. It is best to draw freon samples from the dilution bottles into a syringe to fill the cuvettes. (Freon with a specific gravity of 1.5635 is the bottom phase). Absorbance is then read on the instrument which has been carefully zeroed on clean freon. If the reading exceeds 1000 ppm, appropriate dilutions are carried out with syringes.

EXAMPLE 11

Table 1 contains data from a direct comparison of corrosion rates of a commercial inhibitor and the inhibitor prepared in Example 1, above.

TABLE 1

Summary of Flush Probe Corrosion Data

| Inhibitor | Dosage (ppm) | pH at time of Inhibitor Addition | pH at end of test | ($H_2S$) at end of test (ppm) | Corr. Rate when Inhibitor Added (mpy) | Final[1] Corr. Rate (mpy) |
|---|---|---|---|---|---|---|
| Commercial Inhibitor | 200 | 5.6 | 5.1 | 9.4 | 33.4 | 1.5 |
| Commercial Inhibitor | 200 | 5.5 | 5.4 | 12.3 | 78.6 | 5.3 |
| Inhib. of Example 1 | 200 | 5.5 | 7 | 8 | 23 | 5 |
| Inhib. of Example 1 | 200 | 5.6 | 6.6 | 4.3 | 25 | 12 |

[1]The rates declined to these values within minutes of inhibitor addition.

From these data it is apparent that the inhibitor of Example 1 is comparable to the commercial inhibitors.

Table 2 compares weight loss using commercial inhibitors and the inhibitor of Example 1.

TABLE 2

Summary of Weight Loss Data

| Inhibitor | Dosage (ppm in water phase) | Test Duration (Hrs.) | Corrosion Rate (mpy) | Final pH |
|---|---|---|---|---|
| Blank | — | 20 | 36.2 | 6.5 |
| Commercial Inhib. #1 | 80 | 20 | 6.2 | 7.2 |
| Commercial Inhib. #2 | 80 | 20 | 5.9 | 6.6 |
| Inhib. of Ex. 1 | 80 | 20 | 7.0 | 6.9 |
| Diethylene Triamine | 120 | 20 | 12.7 | 6.6 |
| Ethylene Diamine | 120 | 20 | 9.6 | 6.9 |

The data illustrate that the inhibitor of Ex. 1 is comparable to the commercial inhibitors under equal pH conditions (i.e. the inhibitor of Ex. 1 was neutralized to a pH less than 7 before injection) and is better than the simple amines which are used at a 50 percent higher dosage level. As seen in Table 2, the simple polyamines are added at a dosage of 120 ppm. Thus, reducing the dosage rate to 80 ppm of the other additives would result in even higher corrosion rates than illustrated.

The unique advantage of the inhibitors of the invention, as exemplified by the inhibitor of Example 1, is seen in Table 3 which compares hydrocarbon carryunder of the commercial inhibitor used in Tables 1 and 2 as compared to the low hydrocarbon carryunder of the inhibitor of Example 1.

TABLE 3

Determination of Oil in Water Samples

| Treatment | Waiting Time (min.) | Range of Oil in Water (ppm) | Appearance of Water |
|---|---|---|---|
| 200 ppm of Commercial Inhibitor | 1.5 | 10,850–13,650 | Cloudy |
| 200 ppm of Commercial Inhibitor | 5 | 5,340–7,200 | Cloudy |
| 200 ppm of Inhibitor of Ex. 1 | 1.5 | 360–1,150 | Clear |
| 200 ppm of Inhibitor of Ex. 1 | 5 | 150–300 | Clear |

EXAMPLE 12

Further evidence of low hydrocarbon carryunder of the inhibitors of the invention is illustrated by the data in TABLE 4 which contains data comparing the emulsion tendencies of the inhibitors of the invention (as illustrated by the inhibitor of Ex. 1) with neat polyamines and two commercial inhibitors.

TABLE 4

| Inhibitor | Dosage (ppm) | Oil in Water Phase After 1.5 Min. | After 5 Min. | Appearance of Water |
|---|---|---|---|---|
| Diethylenetriamine | 80 | 2870 | 1328 | Clear |
| Ethylenediamine | 80 | 1955 | 708 | Clear |
| Commercial Inhib. #1 | 80 | 9170 | 6206 | Cloudy |
| Commercial Inhib. #2 | 80 | 11180 | 5355 | Cloudy |
| Inhibitor of Ex. 1 | 80 | 1090 | 348 | Clear |

Examples 11 and 12 illustrate that the inhibitors of the invention are characterized by a unique combination of good corrosion inhibition and low hydrocarbon carryunder. It is contemplated that inhibitors of Examples 2–10 would have characteristics similar to the inhibitor of Example 1.

By low hydrocarbon carryunder, it is meant that the amount of oil in the water phase is below that point at which the water becomes cloudy.

EXAMPLE 13

The inhibitor of Ex. 1 was used in a refinery where severe problems were encountered because of oil carryunder by a commercial corrosion inhibitor. Oil was being carried under into the accumulator water. A field trial was set up and effectiveness was monitored by use of weight loss coupons. The accumulator water had a heavy foam and contained about 4 percent oil after settling. The corrosion rate at the bottom of the accumulator (which reflects corrosion in overhead heat exchangers) was 2–2.5 mpy. Introduction of commercial inhibitor was stopped which caused the corrosion rate to increase to 4.5 mpy but caused the oil in the aqueous phase to drop to 140 ppm after a few hours. Injection of the inhibitor of Ex. 1 at 1.5 times the dosage rate of the commercial inhibitor caused the corrosion rate to drop to 2 mpy after less than one day and caused the oil carryunder to drop to 65 ppm.

The inhibitors of the invention may also be used in the form of their acid salts and quaternary ammonium salts. Thus, the inhibitors of the invention may be used in the form of any water soluble salt which forms an ion pair with the polyamine/formaldehyde reaction products, e.g. chloride, chlorite, sulfide, sulfate, phosphate and the like. Similarly, the quaternary salts of the inhibitor, formed by quaternization with, for example, benzylchloride, methylchloride, dimethylsulfate, dichlorethyl ether and other known quaternizing agents, may be used in the practice of the invention. Although the preferred inhibitors are not quaternized, effective inhibition and low hydrocarbon carryunder are achieved in inhibitors of the invention wherein up to about 10 percent, preferably up to about 5 percent, of available nitrogen atoms are quaternized.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and description set forth herein, but rather that the claims be construed as encompassing all the features of patentable novelty which reside in the present invention, including all features which would be treated as equivalent thereof by those skilled in the art to which the invention pertains.

What is claimed is:

1. Process of minimizing hydrocarbon carryunder while inhibiting corrosion in a chemical industry process water system comprising adding thereto an effective corrosion inhibiting amount of the reaction product of an alkylenepolyamine and formaldehyde, wherein said water system is in an oil refinery.

2. Process of claim 1 wherein said water system is an oil refinery overhead system.

3. Process of claim 1 wherein said alkylenepolyamine is represented by the formula:

$$H_2N-R-NH-R-NH)_xH$$

wherein R represents a hydrocarbon radical of up to about 12 carbon atoms and x represents 0 to about 15.

4. Process of claim 3 wherein said reaction product is in the form of a quaternary salt thereof.

5. Process of claim 3 wherein said reaction product is in the form of an acid salt thereof.

6. Process of claim 3 wherein said alkylenepolyamine is ethylenediamine.

7. Process of claim 6 wherein said reaction product is in the form of an acid salt thereof.

8. Process of claim 6 wherein said reaction product is in the form of a quaternary salt thereof.

9. Process of claim 3 wherein said alkylenepolyamine is diethylenetriamine.

10. Process of claim 9 wherein said reaction product is in the form of an acid salt thereof.

11. Process of claim 9 wherein said reaction product is in the form of a quaternary salt thereof.

12. Process of minimizing hydrocarbon carryunder while inhibiting corrosion in a chemical industry process water system comprising adding thereto an effective corrosion inhibiting amount of the reaction product of an alkylenepolyamine and formaldehyde, wherein said reaction product is in the form of an acid salt thereof.

13. Process of claim 12 wherein said alkylenepolyamine is represented by the formula:

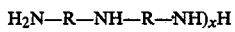

wherein R represents a hydrocarbon radical of up to about 12 carbon atoms and x represents 0 to about 15.

14. Process of claim 13 wherein said alkylenepolyamine is ethylenediamine.

15. Process of claim 13 wherein said alkylenepolyamine is diethylenetriamine.

16. Process of minimizing hydrocarbon carryunder while inhibiting corrosion in a chemical industry process water system comprising adding thereto an effective corrosion inhibiting amount of the reaction product of an alkylenepolyamine and formaldehyde, wherein said reaction product is in the form of a quaternary salt thereof.

17. Process of claim 16 wherein said alkylenepolyamine is represented by the formula:

wherein R represents a hydrocarbon radical of up to about 12 carbon atoms and x represents 0 to about 15.

18. Process of claim 17 wherein said alkylenepolyamine is ethylenediamine.

19. Process of claim 17 wherein said alkylenepolyamine is diethylenetriamine.

* * * * *

UNITED STATES PATENT AND TRADEMARK OFFICE
CERTIFICATE OF CORRECTION

PATENT NO.  : 4,877,578

DATED       : October 31, 1989

INVENTOR(S) : Michael J. Zetlmeisl, et al

It is certified that error appears in the above-identified patent and that said Letters Patent is hereby corrected as shown below:

In Claim 3, delete the formula:

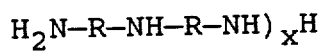

and substitute therefor:

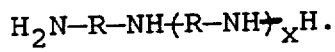

In Claim 13, delete the formula:

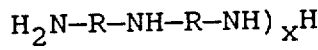

and substitute therefor:

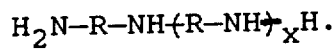

Signed and Sealed this

Twenty-fifth Day of September, 1990

Attest:

HARRY F. MANBECK, JR.

Attesting Officer

Commissioner of Patents and Trademarks